US00PP19746P2

(12) United States Plant Patent
Kordes

(10) Patent No.: US PP19,746 P2
(45) Date of Patent: Feb. 17, 2009

(54) SHRUB ROSE PLANT NAMED 'KORDWARUL'

(50) Latin Name: *Rosa hybrida*
Varietal Denomination: KORdwarul

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 5 days.

(21) Appl. No.: 11/893,515

(22) Filed: Aug. 15, 2007

(51) Int. Cl.
*A01H 5/00* (2006.01)

(52) U.S. Cl. ..... Plt./107
(58) Field of Classification Search ..... Plt./107
See application file for complete search history.

(56) References Cited

U.S. PATENT DOCUMENTS

PP16,849 P2 * 7/2006 Kordes ..... Plt./121

OTHER PUBLICATIONS

UPOV ROM GTITM Computer Database, GTI Jouve Retrieval Software 2008/02 Citation for 'Kordwarul'.*

* cited by examiner

*Primary Examiner*—Wendy C. Haas

(57) ABSTRACT

A new and distinct variety of rose with novel pink flowers, and attractive foliage with good disease resistance. It exhibits moderately vigorous yet compact growth with abundant flowers. The new variety propagates well from cuttings and by grafting. This new and distinct variety has shown to be uniform and stable in the resulting generations from asexual propagation.

2 Drawing Sheets

Latin name of genus and species: The botanical classification of the new rose plant is *Rosa hybrida.*

Variety denomination: The denomination of the new variety is 'KORdwarul'.

BACKGROUND OF THE INVENTION

The new variety of rose plant of the present invention originated from a controlled crossing in a breeding program of two distinct parents during the summer of 1995. The crossing was between two un-named seedlings. The seed parent was the result of a crossing of an 'un-named seedling' and 'KORlima', a non-patented rose variety. The pollen parent was the result of crossing 'KORmarie', a non-patented rose variety and the offspring of an 'un-named seedling' crossed with 'KORgosa', a non-patented rose variety.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORdwarul'.

SUMMARY OF THE INVENTION

The new rose plant may be distinguished from its seed parent, an un-named seedling, by the following combination of characteristics:

1. 'KORdwarul' has small sized violet-pink flowers, while the seed parent has medium sized red flowers; and
2. 'KORdwarul' has excellent disease resistance, while the seed parent has poor disease resistance.

The new rose plant may be distinguished from its pollen parent, an un-named seedling, by the following combination of characteristics:

1. 'KORdwarul' has small leaves and a compact growth habit, while the pollen parent has large leaves and an upright habit; and
2. 'KORdwarul' has small flowers, while the pollen parent has small flowers.

The objective of the hybridization was to create a new and distinct rose plant with unique qualities, such as:

1. Compact and uniform growth and flowering;
2. Abundant attractive, recurrent flowers;
3. Attractive and abundant foliage; and
4. Resistance to diseases encountered in landscapes and gardens.

This combination of qualities is not present in prior rose cultivars. These objectives have been substantially achieved and in that distinguish 'KORdwarul' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORdwarul' was selected in May, 1996 from the seedling beds to be asexually propagated for further evaluation. The first asexual propagation of 'KORdwarul' was done by budding to seedling understocks in July, 1996 at the inventor's nursery in Offenseth-Sparrieshoop, Germany.

This initial and other subsequent propagations conducted in controlled environments demonstrate that 'KORdwarul' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORdwarul'. Specifically illustrated in the first drawing.

Figures 1, 2, 3, 4, 5, 6:
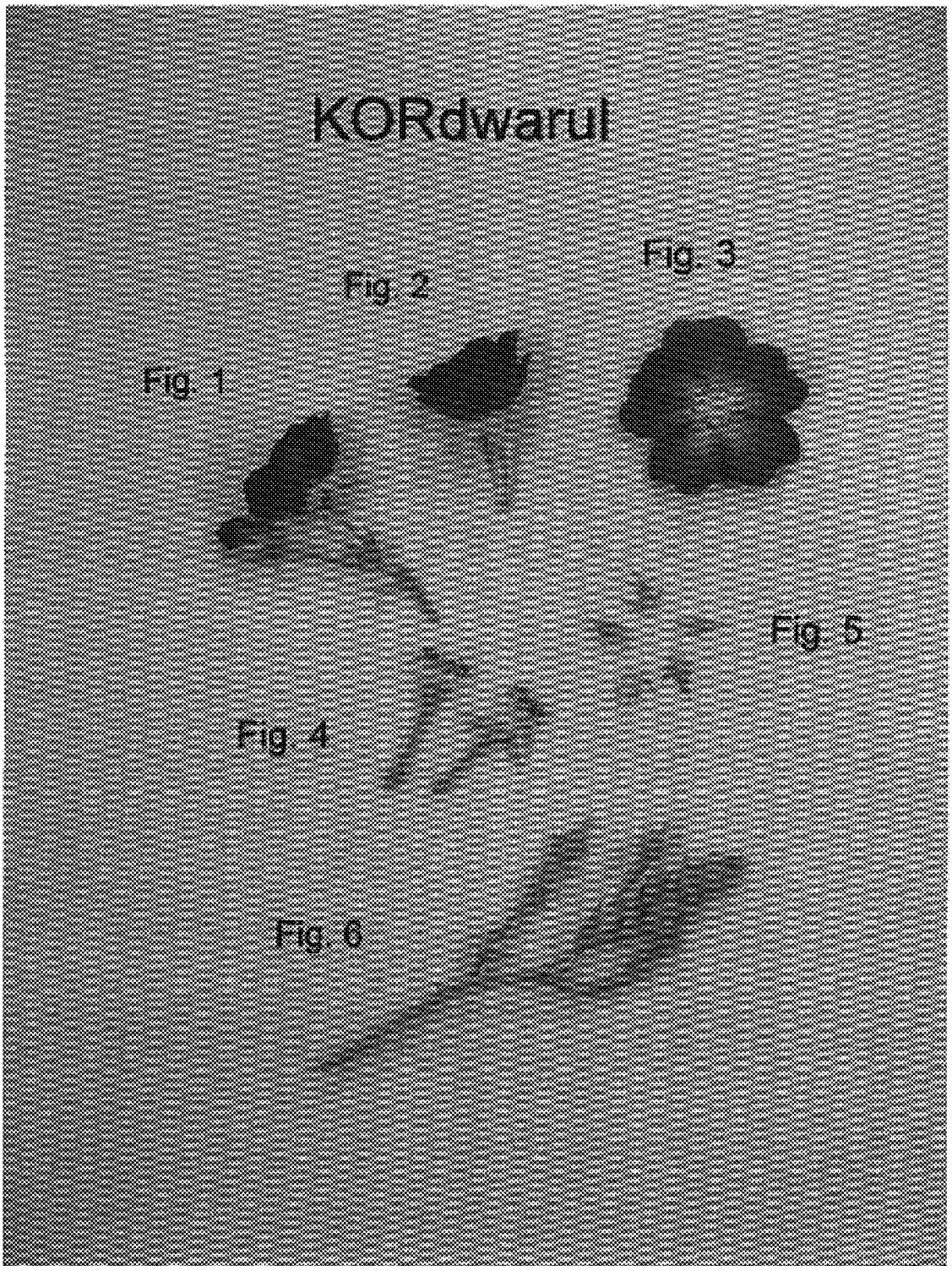
FIG. 1. Flower bud and half opened flower bloom.
FIG. 2. Flower, ⅔ open.
FIG. 3. Open flower.
FIG. 4. Dissected flowers.
FIG. 5. Sepals.
FIG. 6. Tip of flowering stem.
Figures 7, 8, 9:
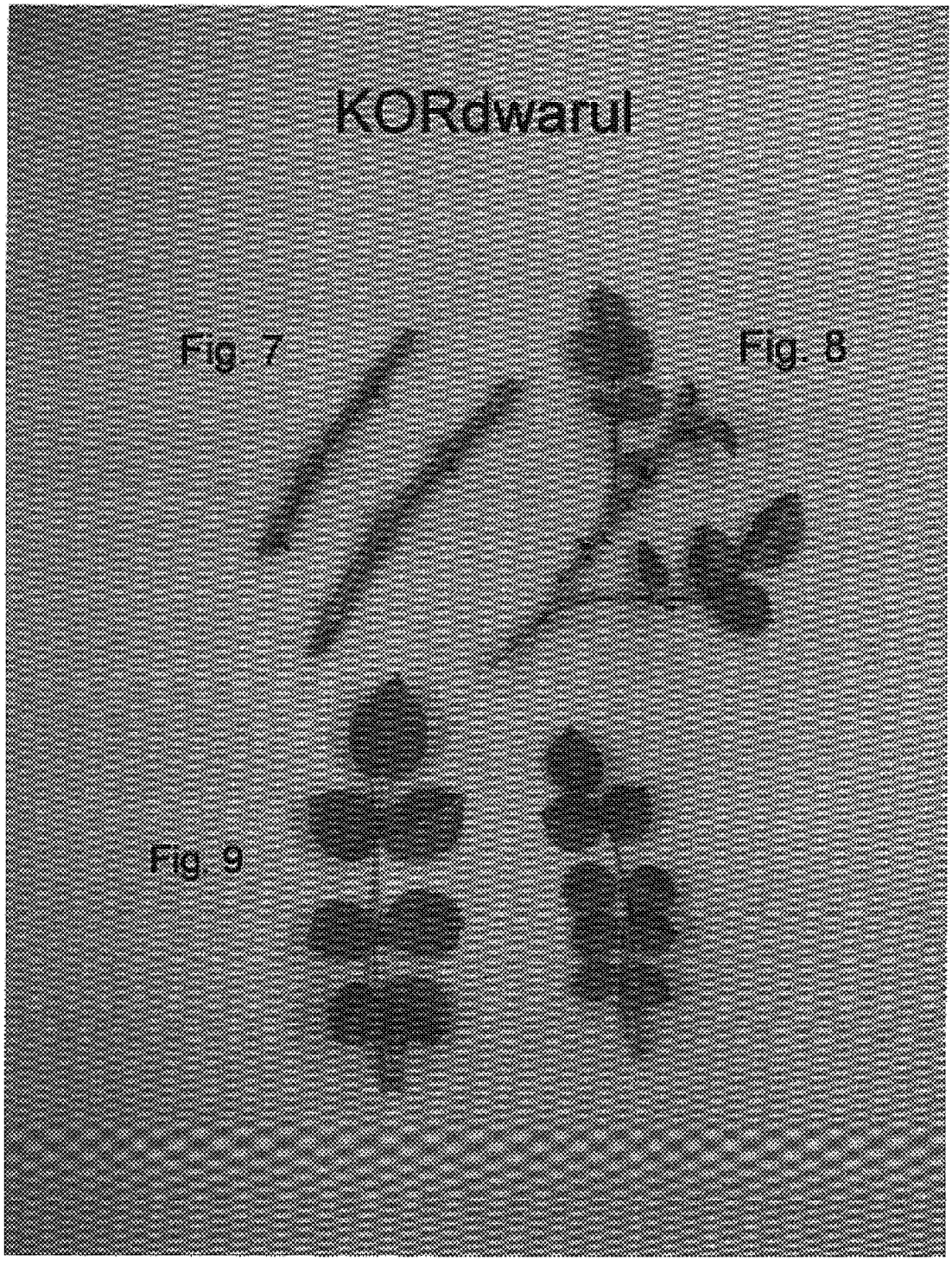

Specifically illustrated in the second drawing:

FIG. 7. Stem exhibiting thorns;

FIG. 8. Distal portion of stem;

FIG. 9. Leaves.

DETAILED BOTANICAL DESCRIPTION

The following is a description of 'KORdwarul', as observed growing in Offenseth-Sparrieshoop, Germany on plants of two years of age. Color references are made using The Royal Horticultural Society (London, England) Colour Chart, 2001 except where common terms of color are used.

For a comparison, several physical characteristics of the rose variety 'KORtufee', a rose variety from the same inventor described and illustrated in U.S. Plant. Pat. No. 16,849 and issued on Aug. 18, 2006 are compared to 'KORdwarul' in Chart 1.

CHART 1

| Characteristic | 'KORdwarul' | 'KORtuffe' |
|---|---|---|
| Petal count. | Single petaled flower with an average of 7 petals. | Very double flower with 45-55 petals. |
| Petal color, ¼ open bloom | Upper surface: Red-Purple Group 60A. Lower surface: Red-Purple Group 60B | Upper surface: Red-Purple Group 67B. Lower surface is: Red-Purple Group 67A. |

Parents:

*Seed parent.*—An 'un-named seedling'.

*Pollen parent.*—An 'un-named seedling'.

Classification:

*Botanical classification.—Rosa hybrida,* 'KORdwarul'.

*Commercial classification.*—Shrub.

FLOWER AND FLOWER BUD

Blooming habit: Recurrent.

Flower bud:

*Size.*—Upon opening, 20 mm in length from base of receptacle to end of bud and 8–10 mm in diameter.

*Bud form.*—Moderately long. Pointed ovoid.

*Bud color.*—As sepals first unfold, bud color is Red-Purple Group 59A. When ¼ open, the upper surface of the petal is Red-Purple Group 60A, and the lower surface is Red-Purple Group 60B.

*Sepals.*—Size: Average 10–12 mm long×5 mm wide. Shape: Sepals generally subulate. Sepal apex is generally pointed. Weak foliaceous appendages on three of the five sepals. Base is flat at union with receptacle. Quantity: Five. Surface texture: Inner side: Covered in fine hairs. Outer surface: Smooth. Stipitate glands are present on margins. Color: Upper surface: Green Group 138A. Lower surface: Green Group 137A.

Receptacle:

*Surface.*—Smooth.

*Color.*—Green Group 138A.

*Shape.*—Urn shaped.

*Size.*—6 mm (h)×3 mm (w).

Peduncle:

*Surface.*—With stipitate glands.

*Length.*—20–25 mm average length.

*Diameter.*—1.0–1.5 mm average diameter.

*Color.*—Green Group 137A. Some with intonations of Greyed-Purple Group 183C.

*Strength.*—Moderately strong.

*Borne.*—Multiple flower buds per stem, generally 15 to 25.

Flower bloom:

*Fragrance.*—Light to moderate fragrance of spice and fruit.

*Duration.*—On the plant 2–3 days. Senesced petals drop away cleanly.

*Size.*—Small flowered garden rose. Average flower diameter is 30 mm when open.

*Form.*—Shape of flower when viewed from the side: Upon opening, upper part: Flattened convex. Upon opening, lower part: Flattened convex. Open flower, upper part: Flattened convex. Open flower, lower part: Flattened convex.

Color:

*Upon opening, petals.*—Outermost petals: Outer Side: Red-Purple Group 60B. Inner Side: Red-Purple Group 61B. Innermost petals: Outer Side: Red-Purple Group 59B. Inner Side: Red-Purple Group 61B.

*Upon opening, basal petal spots.*—On all petals, the color of the basal area transitions from white above to yellow below. Basal petal spot, outermost petals: Outer Side: Yellow Group 1D at base to White Group 157A above, then to petal color. Inner Side: Yellow Group 1D at base to White Group 157A, then to petal color. Basal petal spot, innermost petals: Outer Side: Yellow Group 1D at base to White Group 157A, then to petal color. Inner Side: Yellow Group 1D at base to White Group 157A, then to petal color.

*After opening, petals.*—Outermost petals: Outer Side: Red-Purple Group 61B. Inner Side: Red-Purple Group 61B. Innermost petals: Outer Side: Red-Purple Group 60A. Inner Side: Red-Purple Group 60A.

*After opening, basal petal spots.*—Outer Side: Yellow Group 1D at base to White Group 157A above, then to petal color. Inner Side: Yellow Group 1D at base to White Group 157A, then to petal color. Basal petal spot, innermost petals: Outer Side: Yellow Group 1D at base to White Group 157A, then to petal color. Inner Side: Yellow Group 1D at base to White Group 157A, then to petal color.

General tonality: On open flower Red-Purple Group 60B to 61B. No change in the general tonality at the end of the $2^{nd}$ day. Afterwards, general tonality is Red-Purple Group 61C.

Petals:

*Petal count.*—Single. Approximately 7 petals under normal conditions.

*Petal reflex.*—Petals reflex slightly.

*Petal edge.*—Entire with some undulation.

*Petal shape.*—Apex shape is round. Shape of base is deltoid.

*Petal size.*—10–12 mm long; 10–12 mm wide.

*Thickness.*—Average.

*Petal arrangement.*—Generally in a regular pattern with overlapping edges.

*Petaloids.*—Present. Average of 0–2 per flower. Petaloids are 8 mm long and 3 mm wide. Color of inner side is Red-Purple Group 61B. Color of outer side is Red-Purple Group 61B. Surface texture is smooth. Shape is linear.

Reproductive organs:

*Pistils.*—Approximately 15–20 present. Stigmas: Location: Slightly inferior in position to anthers. Color: Yellow-Green Group 147D. Styles: Length: 4–5 mm long. Color: Yellow-Green Group 147D.

*Stamens.*—Approximately 60–70 on average and regularly arranged. Anthers: Size: 4–5 mm long. Color: Yellow-Orange Group 21C. Pollen: Limited amount present. Color: Yellow-Orange Group 21C. Filaments: Color: Yellow-Green Group 151D. Length: 4–5 mm.

*Seed hips.*—Forming abundant numbers of seed hips. Color: Yellow-Green Group 146B with intonations of Greyed-Purple Group 183C. Size: 6 mm high×4–5 mm wide.

THE PLANT

*Plant growth.*—Moderately vigorous. Bushy habit. Floriferous. When grown as a budded nursery plant the average plant height is 60 cm and the average plant width is 60 cm.

*Stems.*—Stem color: Young wood: Green Group 138A. Older wood: Green Group 138A. Stem surface: Young wood: Smooth. Older wood: Smooth.

*Prickles.*—Present. Incidence: 7–8 per 10 cm of stem. Size: Average length: 5–6 mm. Color: Immature prickles: Greyed-Red Group 181A. Mature prickles: Greyed-Orange Group 174C. Senescing to Greyed-Orange Group 173D. Anthocyanin present on juvenile prickles. Greyed-Red Group 181A on entire thorn. Shape: Linear to deeply concave.

*Leaves and leaflets.*—Normally 7 leaflets on normal leaves in middle of the stem. Leaf size: 95 mm (l)×35 mm (w). Quantity: Abundant. Texture: Semi glossy. Smooth. Leathery. Color, mature foliage: Upper Leaf Surface: Green Group 137A. Lower Leaf Surface: Green Group 138A. Color, juvenile foliage: Upper Leaf Surface: Green Group 137A. Lower Leaf Surface: Green Group 138A. Anthocyanin intonation: Present. Location: Intonations present on juvenile prickles, leaf rachis, stipules, and developing leaflets.

*Stipules.*—Size: 20 mm (l)–10 mm (w). Stipule color: Green Group 137A. Anthocyanin on juvenile stipules of Greyed-Purple Group 183C. Presence of stipitate glands: Present on margins. Margins: Bearded. Serrated.

*Petiole.*—Length: 13–15 mm. Diameter: 1.5 mm. Petiole color: Green Group 137A. Anthocyanin present on juvenile tissue. Prickles: Average of 5–6 small prickles underneath per leaf. Stipitate glands: Stipitate glands on margins.

*Petiole rachis.*—Length: 13–15 mm. Diameter: 1.5 mm. Color: Green Group 137A. Anthocyanin present on juvenile tissue. Greyed-Purple Group 183C. Margins: With stipitate glands. Prickles: A few small prickles underneath. Stipitate glands: Limited numbers of stipitate glands on margins.

*Leaflets.*—Size: Average size of the terminal leaflet is 30 mm (l)×22 mm (w). Leaflet shape: Base: Ovate. Apex: Broadly ovate. Margins: Finely serrated. Texture: Thick. Semi-glossy. Smooth.

Hips/seed formation: Forms hips readily. Shape: Globular. Height: 8–10 mm. Diameter: 8–10 mm. Color: Green Group 138A changing to Greyed-Orange 169A. Senescing to Greyed-Red Group 180A. Persisting.

Winter hardiness: To date, the variety has been grown successfully in Zone 5.

Disease resistance: Above average resistance to powdery mildew, rust, black spot and Botrytis rose diseases under normal growing conditions.

I claim:

1. A new and distinct variety of rose plant characterized by the following combination of characteristics:

(a) forms attractive, long lasting pink flowers;

(b) exhibits a uniform bushy growth habit;

(c) propagates well using traditional methods, and;

(d) exhibits very good resistance to disease under normal growing conditions;

substantially as herein illustrated and described.

* * * * *

KORdwarul

KORdwarul